(12) United States Patent
Raghavan et al.

(10) Patent No.: US 8,582,397 B2
(45) Date of Patent: Nov. 12, 2013

(54) CREATING, DIRECTING AND STEERING REGIONS OF INTENSITY OF WAVE PROPAGATION IN INHOMOGENEOUS MEDIA

(75) Inventors: Raghu Raghavan, Baltimore, MD (US); Timothy Poston, Bangalore (IN)

(73) Assignee: Therataxis, LLC, Baltimore, MD (US)

( * ) Notice: Subject to any disclaimer, the term of this patent is extended or adjusted under 35 U.S.C. 154(b) by 461 days.

(21) Appl. No.: 12/945,048

(22) Filed: Nov. 12, 2010

(65) Prior Publication Data

US 2011/0060271 A1 Mar. 10, 2011

Related U.S. Application Data

(63) Continuation-in-part of application No. 12/991,756, filed as application No. PCT/US2009/002919 on May 12, 2009, which is a continuation-in-part of application No. 12/319,311, filed on Jan. 6, 2009.

(51) Int. Cl.
 *G10K 11/34* (2006.01)
(52) U.S. Cl.
 CPC ................................... *G10K 11/346* (2013.01)
 USPC .......................................................... 367/138
(58) Field of Classification Search
 USPC .......................................................... 367/138
 See application file for complete search history.

(56) References Cited

U.S. PATENT DOCUMENTS

| | | | | |
|---|---|---|---|---|
| 5,092,336 A | * | 3/1992 | Fink | 600/443 |
| 5,428,999 A | * | 7/1995 | Fink | 73/599 |
| 5,752,515 A | * | 5/1998 | Jolesz et al. | 600/458 |
| 7,101,337 B2 | * | 9/2006 | Aubry et al. | 600/447 |
| 2004/0054282 A1 | * | 3/2004 | Aubry et al. | 600/437 |
| 2004/0267234 A1 | * | 12/2004 | Heart et al. | 604/500 |
| 2005/0277824 A1 | * | 12/2005 | Aubry et al. | 600/407 |
| 2006/0241529 A1 | * | 10/2006 | Hynynen et al. | 601/2 |
| 2007/0127315 A1 | * | 6/2007 | Tompkins | 367/75 |
| 2009/0034756 A1 | * | 2/2009 | Volker et al. | 381/119 |
| 2009/0185444 A1 | * | 7/2009 | Kluver | 367/24 |
| 2009/0270790 A1 | * | 10/2009 | Raghavan | 604/22 |
| 2010/0018718 A1 | * | 1/2010 | Krebs et al. | 166/369 |
| 2010/0067328 A1 | * | 3/2010 | Curtis | 367/50 |
| 2011/0106009 A1 | * | 5/2011 | Solar et al. | 604/122 |

OTHER PUBLICATIONS

Andrew Curtis et al., Seismic interferometry-turning noise into signal, The Leading Edge, Sep. 2006, pp. 1082-1092.

* cited by examiner

*Primary Examiner* — Isam Alsomiri
*Assistant Examiner* — James Hulka
(74) *Attorney, Agent, or Firm* — Mark A. Litman & Associates, P.A.

(57) ABSTRACT

Known time reversal methods consist of three steps which may be listed as (i) the recording of signals and (ii) the time reversing of the recorded signals, and (iii) the transmission of the time-reversed signals. The first and third steps of the above process are retained, but the second step is modified. The empirical signal is transformed to fit mathematical forms taught by the mathematics of singularity and catastrophe theory that ensure a structural stability to the waveforms that will be received, when the time reversed signals are transmitted again. This structural stability ensures robustness of the waveform and the predominant direction of the flux of energy of the waveform, and improves controllability of the location of the high magnitude regions of the energy flux despite limited knowledge of the exact properties of the medium. Applications to drug delivery in the brain, and geophysical applications are envisaged.

16 Claims, 8 Drawing Sheets

CREATING, DIRECTING AND STEERING REGIONS OF INTENSITY OF WAVE PROPAGATION IN INHOMOGENEOUS MEDIA

RELATED APPLICATION DATA

This application is a continuation-in-part application of U.S. Ser. No. 12/991,756, filed 9 Nov. 2010, which claims direct priority and priority through PCT application No. PCT/US2009/002919 International Filing Date of May 12, 2009 as a continuation-in-part of U.S. patent application Ser. No. 12/319,311, filed 6 Jan. 2009.

BACKGROUND OF THE INVENTION

1. Field of the Invention

This invention relates to the field of controlling the intensity of waves in inhomogeneous media, with particular but not exclusive application to the case of sound waves used to guide materials in porous media and other inhomogeneous media.

This application continues to refer to the suite of applications and the several embodiments of this invention in the field of guidance and control of the flow of materials in porous media under the generic term Acoustic Shepherding.

2. Background of the Art

Chemotherapeutic agents are injected into the body with the intent of treating disease. For example, biologically active materials may be injected into the body with the goal of killing or deactivating cells within a tumor mass. Such materials can also be injected or infused in solution into the brain to treat cancer. A problem arises since the infusate may not flow efficiently along an internal body path that leads directly to the targeted mass. Moreover, the target itself may finally be reached after an unacceptably prolonged period because of natural delays in passive diffusion or uncontrolled flow of body fluids. These delays are particularly important in the long term, since endogenous bulk flow is likely to be a significant method of transmission of molecules and even cells in the presence of injury such as edema from tumors, trauma, or hemorrhagic stroke. Such edema cause significant opening of the extracellular spaces along the tracts of white matter such as the corpus callosum, optical fiber tracts, and so on and these provide flow paths for the introduced therapeutic particles that are only temporarily open. Another disadvantage of direct infusion is that, short of chemical intervention (with undesired and potentially dangerous side effects), the characteristic distance over which the pressure and the velocity are not negligible is dependent on the distribution of blood vessels and on the permeability to hydrophilic plasma proteins which are outside the control of the infusion system parameters, thus leaving only the flow rate or the pressure of the infusion alone to drive the fluid. Of course, these driving factors too have a very limited range over which they may be varied, since too low a flow rate means that the distribution of the therapeutic molecule will be dominated by diffusion and loss, resulting in poor spread; while too high a flow rate might mean disruption to brain processes and architecture, and loss of infusate through white matter or CSF pathways.

Ultrasound methods have been used both for imaging and therapy. Most pertinent to this invention have been reports on the enhancement of drug penetration into the brain when catheterization procedures introducing drug into the blood vessels have also included ultrasound irradiation at diagnostic or higher levels: increased penetration of the drug into the brain has been noted. Such studies have been focused on opening the blood brain barrier.

In other art, the phenomenon known as acoustic streaming has been known for more than a century, following the pioneering treatment of Lord Rayleigh. Acoustic streaming is due to dissipation of acoustic wave energy and momentum in a medium, and the induced fluid velocity depends on the mechanism of dissipation. In a medium such as the brain, with compressible compartments, extracellular fluid with narrow channels, and so on, it is expected that a variety of mechanisms will contribute to the overall streaming. As a simple illustrative example, consider a streaming velocity V in the direction of propagation of an acoustic signal. In magnitude, it has the form $V = A\alpha I/\mu c$ where A is a number that depends on details of the boundary conditions and geometries of the problem, $\alpha$ is the attenuation coefficient of the acoustic intensity at the frequency in question, I is the intensity of the sound wave at the point in question, $\mu$ is the viscosity of the fluid, and c is the velocity of sound. The attenuation coefficient $\alpha$ is frequency dependent, often increasing linearly or quadratically with frequency, depending on the pertinent attenuation mechanism.

If a number of mechanisms contribute to the overall dissipation of energy, each of these mechanisms will contribute to a streaming velocity. Thus the actual magnitudes and directions of streaming velocity in the brain calls for an appropriate protocol, such as hand-in-hand development of experimental test and theoretical setup of the equations of fluid flow in a porous medium subject to acoustic irradiation, that can be solved only via computer analysis of the acoustic equations.

To summarize, while direct injection into brain parenchyma is being used, and usefully bypassing the blood-brain barrier to penetration of drugs intended to act in the Central Nervous System (CNS), the resulting drug distribution is difficult to control. Ultrasound has been tested for affecting the permeability of the blood brain barrier, and acoustic streaming has been known in the theory of porous media studied by civil engineers and those skilled in like arts. Time reversal and related techniques based on the reciprocity of the Green function in equations describing wave propagation have been proposed and developed, especially by Mathias Fink et al., for medical applications related to destroying select targets within tissue and especially brain tissue. The following paragraph gives further references to the background art.

The explanation, apparatus enablement, and background on ultrasound (acoustic) enhancement of mass flow, of reversible opening of the blood brain barrier, of time reversal techniques, ultrasound emission and the like are described for example in "Acoustic Enhancement of Diffusion in a Porous Material," Haydock, David and Yeomans, J. M., *Ultrasonics*, 41, (2003) 531-538; "The Mechanism of Generation of Acoustic Streaming," Mitome, Hideto, Electronics and Communications in Japan, Part 3, Vol. 81, No. 10, 1998; "Non-Invasive, Transcranial and Localized Opening of the Blood-Brain Barrier using Focused Ultrasound in Mice," *Ultrasound in Med. & Biol.*, Choi, James J. et al., Vol. 33, No. 1, pp. 95-104, 2007; "Time-Reversal Acoustics in Biomedical Engineering," Fink, Matthias, et al., *Annu. Rev. Biomed. Eng.*, 2003, Vol. 5, pp. 465-497; "Spatio-Temporal Coding in Complex media for Optimum Beamforming: The Iterative Time-Reversal Approach," Montaldo, Gabriel, et al., *IEEE Transactions on Ultrasonics, Ferroelectrics, and Frequency Control*, Vol. 52, No. 2, February 2005; "Experimental Demonstration of Non-Invasive Transskull Adaptive Focusing Based on Prior Computed Tomography Scans," Aubrey, J. F. et al., *J. Acoust. Soc. Am.*, 113, (1), January 2003; "Adaptive Focusing for Transcranial Ultrasound Imaging Using Dual Arrays," Vigno, F. et al., *J. Acoust. Soc. Am.*, 120, (5), November 2006; "High Power Transcranial Beam Steering for Ultrasonic Brain Therapy," Pernot, M. et al., *Phys. Med. Biol.*, 48 (2003) 2577-2589; "Prediction of the Skull Overheating During High Intensity Focused Ultrasound Transcranial Brain Therapy," Pernot, M. et al., 2004 IEEE Ultrasonics Symposium, pages 1005-1011; "Time Reversal of Ultrasonic Fields—Part I: Basic Principles," Fink, Mathias, *IEEE Transactions on Ultrasonics, Ferroelectrics, and Frequency Control*, Vol. 39, No. 5, September 1992; "Time Reversal of Ultrasonic Fields—Part III: Theory of the Closed Time-Reversal Circuit," Cassereau, Didier and Fink, Mathias, *IEEE Transactions on Ultrasonics, Ferroelectrics, and Frequency Control*, Vol. 39, No. 5, September 1992; "Time Reversal of Ultrasonic Fields—Part III: Theory of the Closed Time-Reversal Circuit," Cassereau, Didier and Fink, Mathias, *IEEE Transactions on Ultrasonics, Ferroelectrics, and Frequency Control*, Vol. 39, No. 5, September 1992; "Optimal adaptive focusing through heterogeneous media with the minimally invasive inverse filter," Vignon, Francois and de Rosny, Julien and Aubry, Jean-Francois and Fink, Mathias, *Journal of the Acoustical Society of America*, Vol. 122, No. 5, November 2007, pages 2715-2724; "Spatial and temporal concentrating of energy in ultrasound systems by single transmitter using time-reversal principles," Sarvazyan, A. and Sutin, A., *Proceedings of World Congress on Ultrasonics*, Paris, pp. 863-866, Sep. 7-10, 2003: See also further material by Dr. Sarvazyan and his colleagues at the web site of Artann laboratories www.artannlabs.com; "Patterns of Thermal Deposition in the Skull During Transcranial Focused Ultrasound Surgery," Connor, C. W. and Hynynen, K., *IEEE Transactions on Ultrasonics, Ferroelectrics, and Frequency Control*, Vol. 51, No. 10, October 2004; and Published U.S. Patent Application 2004/0267234. "Brain Arterioles show more active vesicular transport of blood-borne tracer molecules than capillaries and venules after focused ultrasound-evoked opening of the blood-brain barrier", Sheikov, Nickolai and McDannold, Nathan and Jolesz, Ferenc and Zhang, Yong-Zhi and Tam, Karen, and Hynynen, Kullervo, *Ultrasound in Medicine and Biology*, vol. 32, pp 1399-1409 (2006). "Local and Reversible blood-brain barrier disruption by non-invasive focused ultrasound at frequencies suitable for trans-skull sonications", Hynynen, Kullervo and McDannold, Nathan and Sheikov, Nickolai and Jolesz, Ferenc and Vikhodtseva, Natalia *NeuroImage*, vol. 24, pp 12-20 (2005). Hynynen, Kullervo and McDannold, Nathan and Vikhodtseva, Natalia and Jolesz, Ferenc, Radiology, vol. 220, pp 640-646 (2001). "Spatio-temporal analysis of molecular delivery through the blood-brain barrier using focused ultrasound", Choi, J. J. and Pernot, M. and Brown, T. R. and Small, S. A. and Konofagou, E. E., *Physics in Medicine and Biology*, vol. 52, pp 5509-5530 (2007). "Piezo-electric materials for high frequency medical applications: a review", Shung, K. K. and Cannata, J. M. and Zhou, Q. F., *Journal of Electroceramics*, vol. 19, pp 139-145 (2007). "Unified Green's function retrieval by cross-correlation: connection with energy principles", Snieder, Roel and Wapenaar, Kees and Wegler, Ulrich, *Physical Review E* vol. 75 036103-1-14 (2007). These references are incorporated herein in their entireties to provide technical information in support of the present disclosure and claims. Another prominent worker in the field of time reversal acoustics is Armen Sarvazyan and his team at Artann laboratories.

U.S. Pat. No. 5,752,515 (Ferenc A. Jolesz and Kullervo Hynynen) discloses a method and apparatus for directly applying ultrasound for the purposes of opening up the blood-brain barrier (sonoporation) and confirming the opening by the injection of a contrast agent observable with radiological imaging that is visible when the blood brain barrier is compromised. This, and other patents with Kullervo Hynynen as inventor, allow for the transducer to be placed adjacent to brain tissue, by the process of drilling a bore hole through the skull, to obviate the highly distorting effects of the skull.

U.S. Pat. No. 5,092,336 (Mathias Fink) discloses how to localize a reflective target within tissue by the application of ultrasound transmission from transceivers placed distally from the desired target, and subsequent application of time-reversal technology to process the signals reflected from the target, so that an ultrasound beam may be formed for the purposes of focusing the energy on the reflective target.

U.S. Pat. No. 5,428,999 (Mathias Fink) discloses further methods and processing schemes within the rubric of time reversal methods to localize reflective targets in tissue for the purposes of focusing ultrasound on these targets for therapeutic purposes.

U.S. Pat. No. 7,101,337 I(Jean-Francois Aubry, Mathias A. Fink, Mickael Tanter, and Jean-Louis Thomas) discloses a method for imaging, for example, brain tissue allowing for the dissipative heterogeneous acoustic properties of the skull, wherein the transceivers are outside the skull, acoustically coupled to it, and methods of signal processing are introduced to correct for the distortions produced by the skull so that the acoustic signals may propagate through the tissue and be received and decoded for imaging purposes.

U.S. Patent Application Publication 2004/0267234 "Implantable Ultrasound systems and methods for enhancing localized delivery of therapeutic systems" (Gill Heart and Axel Tolkowsky and Joe Brisken) discloses the application of intraparenchymal delivery of a therapeutic agent in solution, with an ultrasound transmitter inserted through a burr hole in the skull to the surface of the brain, coaxial with a catheter that is pumping the therapy-containing solution. The transmitted ultrasound then induces a further spread of the agent, beyond what would be obtainable from the pressure-driven infusion of the solution alone.

U.S. Patent Application Publication 2005/00277824 "Non-invasive method of obtaining a pre-determined acoustic wave field in an essentially uniform medium which is concealed by a bone barrier, imaging method and device for carrying out said methods" (Jean-Francois Aubry and Mathias Fink and Mickael Tanter) teaches a method for obtaining a desired sound field within the brain by means of echographic signal processing methods applied to signals transmitted and received by transceiver arrays positioned outside the skull.

U.S. Patent Application Publication 2006/0241529 "Adaptive Ultrasound Delivery System" (Kullervo Hynynen and Nathan McDannold) discloses a phased array of transceivers, the frequencies and positioning of which are adjusted till the desired opening of the blood brain barrier is achieved, as detected by contrast agent imaging.

All references cited are incorporated herein by reference in their entirety to support the technical nature of the disclosure, as well as those applications and publications from which priority is claimed in the section Related Applications Data.

SUMMARY OF THE INVENTION

This invention, within the field of wave propagation in inhomogeneous media, introduces methods for creating high intensity regions with planned directions for the intensity vector of the waves; and methods for steering such regions and directions within the said inhomogeneous media. The waves can be acoustic or electromagnetic. The methods introduced ensure the stability of the intensity patterns that are created as the inhomogeneity encountered by the wave is varied, in contrast to previous different methods for creating such regions of high intensity by time reversal of the waves referred to in the referenced art.

DETAILED DESCRIPTION OF THE INVENTION

Figure 1:
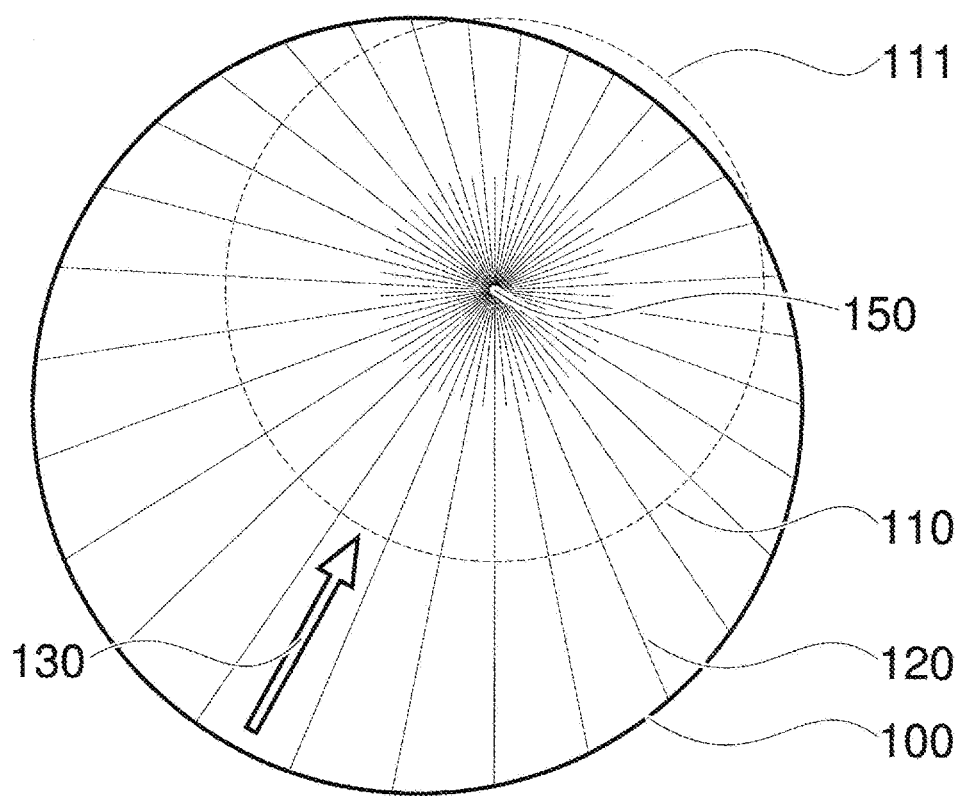
FIG. 1 shows a focus obtained in the limit of ray propagation from signals transmitted from an array of transmitters entirely surrounding the focus.

The subject of this technology is a significant improvement in the control of intensity at a quality desirable in practicing the technology disclosed in U.S. patent application Ser. No. 12/319,311, filed 10 Jan. 2010, which is incorporated herein by reference in its entirety, and applicable to a range of other uses of localized wave intensity in inhomogeneous media.

Time reversal methods have been used to focus acoustic waves within the brain. A frequently used method (Sarvazyan references in original patent application) is to emit a signal from a point P, and record at another point Q the received signals over a considerable length of time that includes multiple reflections from within the skull. (Typically, one of the points P and Q is internal to the brain, while the other is on near its boundary.) If the original signal emitted at P is a sharp pulse, the received signal may be called an empirical Green function as evaluated at Q. (Mathematically, the complete Green function includes values at points throughout the region of interest.) Then, this Green function is time reversed and re-transmitted from one of the points P and Q, in which case the signals recombine in phase after a characteristic time and result in a sharp pulse at the other of the two points. Despite significant leading and trailing signals, this method can be used to compress energy into a shorter time interval than the time interval used in the original signal collection phase. With one or more transmitters, each with its own recorded function of signal over time, this provides a sharp focus within an inhomogeneous medium. A recent article that describes this technique and some results is [Matthias Fink: "Time reversed waves in complex media", pages 146-168 in the book "New Directions in Linear Acoustics", Matthew Wright and Richard Weaver, editors, Cambridge University Press 2010]. In contrast, it is possible to achieve a focus at a point F by the use of a single datum for each point A from which emission is planned (the time of the shortest travel path between A and F), provided a sufficiently closely spaced array of emitters at such points A. Pulses emitted from the different points A in time-reversed order from the arrival of the leading edge of the signal from F combine by Huyghens' Principle to create a wavefront that collapses to the point F, with resulting high intensity. Unlike the Green function method, this process of using an array of transmitters near the point A makes essential use of interference between signals from neighboring points A; a pulse from a single such point, unlike a signal varied over substantial time as just considered, has no special relation with F more than any other point. The Green function method can be reinforced by using a multiple array of points A, each such point A emitting its own time-reversed signal, but does not require it.

The emission of pulses from the points A in a particular temporal relationship, resulting in a single focused pulse at point F, can be replaced by emission of a continuous wave signal from the points A in a particular phase relationship, resulting in a steady focus of pulses at point F, by means familiar to those skilled in the art. (See the literature on phased arrays in acoustics, for example Introduction to Phased Array Ultrasonic Technology Applications, R/DTech Inc. [now Olympus NDT], 2004.)

FIG. 1 shows a simple two-dimensional example of a focus where the wavefronts impinge from all directions. A pulse is emitted from each point on the set 100 of emitters, at the time when a wavefront drawn as the dashed curves 110 and 111 would cross it. (In the continuous formulation, the same curves 110 and 111 represent a set of points over which at a particular moment the phase is constant.) The result is that a physical wavefront comes into existence as the theoretical wavefront crosses the set 100. In the 'snapshot' example shown, the part 110 of the wavefront inside the set 100 exists as a physical wave, while the part 111 of the wavefront outside the set 100 does not yet have physical reality. Rays 120, drawn orthogonal to the wavefront 110 at each point it passes through (which makes them radial to the point 150), capture the motion of the wavefront 110 through a range of time (rather than just a single-time snapshot) and make clear the spatial concentration of wave energy: in this case, with perfect collapse of the wavefront 110 at the focus point 150. The rays drawn are arbitrarily truncated a little beyond the point 150, though the physical propagation continues, and echoes (for example, from the skull) may produce complicated patterns of varying intensity, usually much less than the intensity at an intentional 'hot spot' like the point 150. The figures below use the same ray representation, for clarity, rather than the wavefronts.

The figures show straight ray paths, corresponding to wave propagation in a perfectly homogeneous medium, but time reversal methods (whether by the Green function approach or by the wavefront synthesis used here) are equally applicable to any waves in a linear medium with low attenuation, even if it is inhomogeneous, anisotropic, or dispersive. The arrows in each figure show the general direction of flow along the rays, distinguishing 'forward' from 'backward': transport along the ray nearest the arrow is in the direction near to the arrow direction, rather than nearly opposite, and continuity of direction between neighboring rays gives the direction of transport along the rest.

Figure 2:
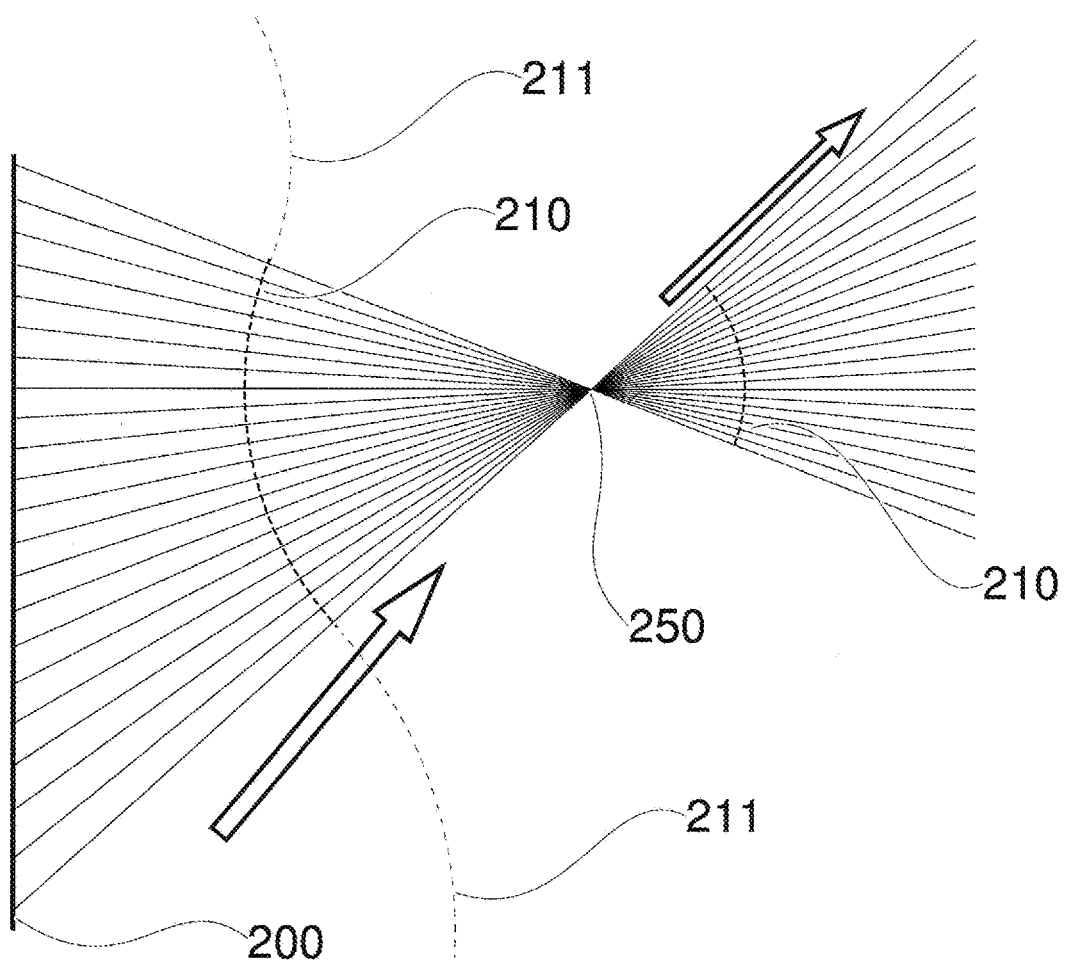
FIG. 2 shows a "perfect focus" in the ray propagation limit of waves emitted from a line of transmitters.

FIG. 2 shows an example, also in a homogeneous medium, which focuses rays emitted from a line 200 of transmitters in a two dimensional illustration, and propagated to the right. Appropriate timing of the wavefront emission from points of the line of transmitters 200 arranges that the main wavefront 210 is initially concave, passing through a focus point 250 and then growing as a convex shape. (Huyghens' Principle also gives fronts 211 expanding from the boundaries of the emitter array 200, but these are weak and of little importance here.) Since the waves, which focus at the point 250 in the ray-theoretic limit, come predominantly from the left in the diagram, the streaming force in the acoustic case due to the attenuation of the waves will also be in the direction of propagation of the waves (i.e., to the right) in the absence of obstacles and nearby boundaries. This streaming force will be a maximum near the ray-theoretic focus: the true maximum when wave theory and the finite aperture of the transmitters is taken into account will of course not coincide with the geometric focus, or achieve the infinite value implied by strict ray theory, but it will be close to the point 250 shown. A good description of the 'Pearcey function' intensity pattern of finite-wavelength radiation in the vicinity of a cusp point, for the acoustic case, may be found in [R. Marchiano, F. Coulouvrat, J.-L. Thomas: <<Nonlinear focusing of acoustic shock waves at a caustic cusp>>, J. Acoust. Soc. Am., 117, 566-577, 2005].

The appropriate emission timing to achieve a perfect focus like the point 250 is easily computed for the case of a homogeneous medium, and the corresponding wave-theoretic peak is well realized if this timing is implemented, but an imperfectly known inhomogeneous medium presents much greater problems. In the inventive steps below we replace 'perfect' focusing by intensity structures that are more robust, and more practical to target given limited data about the medium.

We replace the Green function process of collection of complete signals by recording only the time delay of the leading edge of the received signal, and using these in the inventive steps described below. This will apply whether or not a directional force is required at the hot spot. The two cases where such a force is required (or not) are distinguished in the description below.

We refer to the assignment of a pulse emission time T(A) to each emission point A in the line array 200 as an 'emission timing function', treated for the following discussion as a continuous function of the point A (though practical embodiment replaces this by a closely spaced finite set. We can take derivatives of this function with respect to the location A, either by directly using differences between times measured for neighboring points A, or by formally differentiating a smooth formula fitted to the measured data. In what follows a 'derivative' has the meaning common among mathematicians, of an approximating function, rather than a number such as slope. Thus, the first derivative of a function at a point P is the best available linear approximation to the function that is good near P, the second derivative is the quadratic approximation to the difference between the function and its linear approximation, and so on. These derivatives are in practice specified by one or more numbers (derivatives or partial derivatives, in the sense of introductory Calculus), arranged in arrays such as row vectors and matrices, but they do not constitute numbers. They may be more accurately thought of as the linear part of the Taylor expansion at P (in as many variables as are relevant) to the function, the quadratic part, and so on. In the present use the point P is the location A within the curve or surface of emission points, and the partial derivatives used in a Taylor expansion are with respect to the number u or numbers u and v used to label points within that curve or surface, in the way that Latitude and Longitude (or other pairs of numbers) label points on a sphere. In the case of a surface, therefore, to match a first derivative at a point is to control the two coefficients a and b in an expression au+bv, to match a second derivative is to control the three coefficients in $au^2+buv+cv^2$, and so on.

Figure 3:
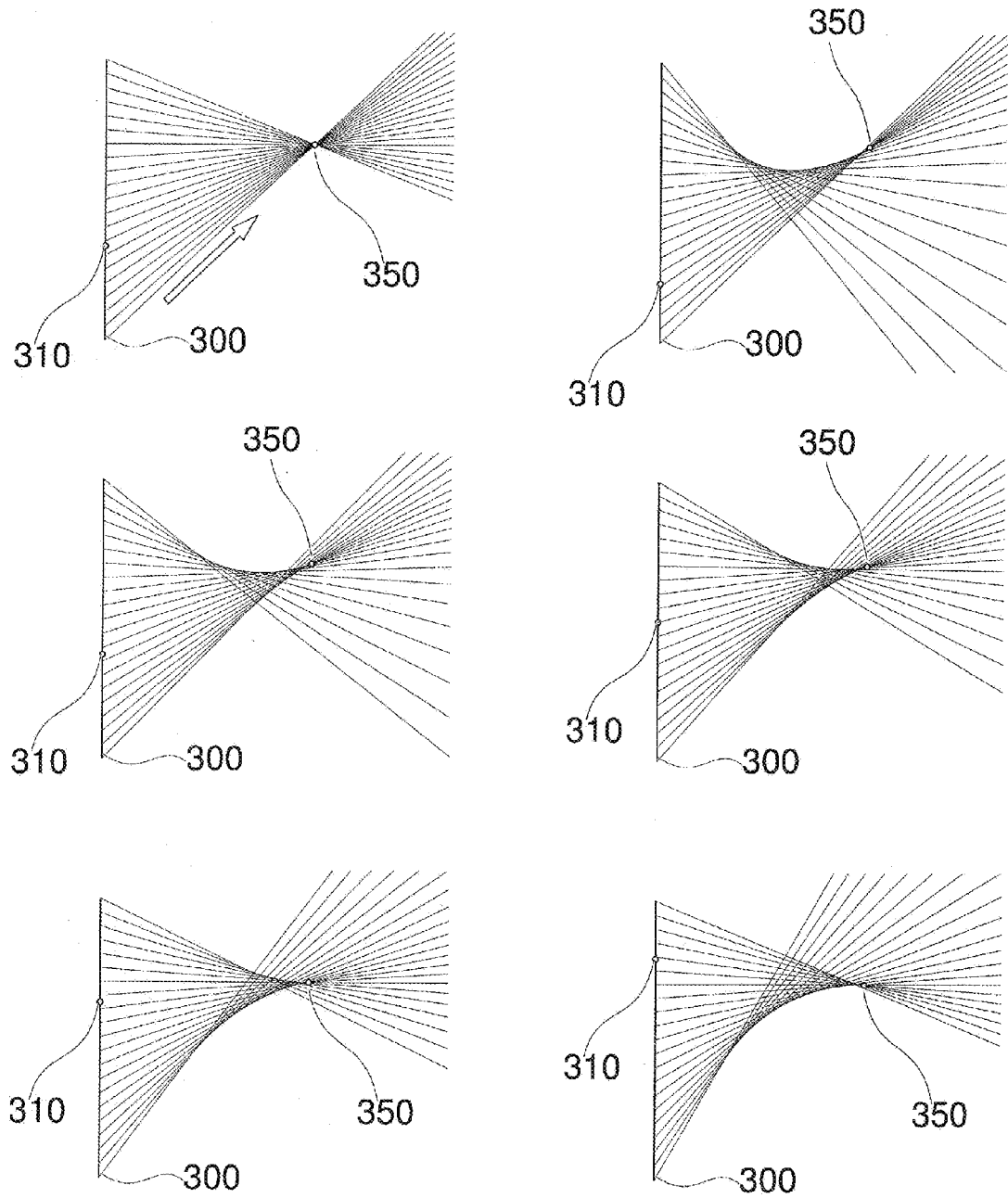
FIG. 3 shows the results of a low dimensional, here linear, approximation to FIG. 2 by matching Taylor expansion around different array points of the timing of the transmitted signals as a function of transmitter location, resulting in a structurally stable caustic profile with a cusp point.
Figure 4:
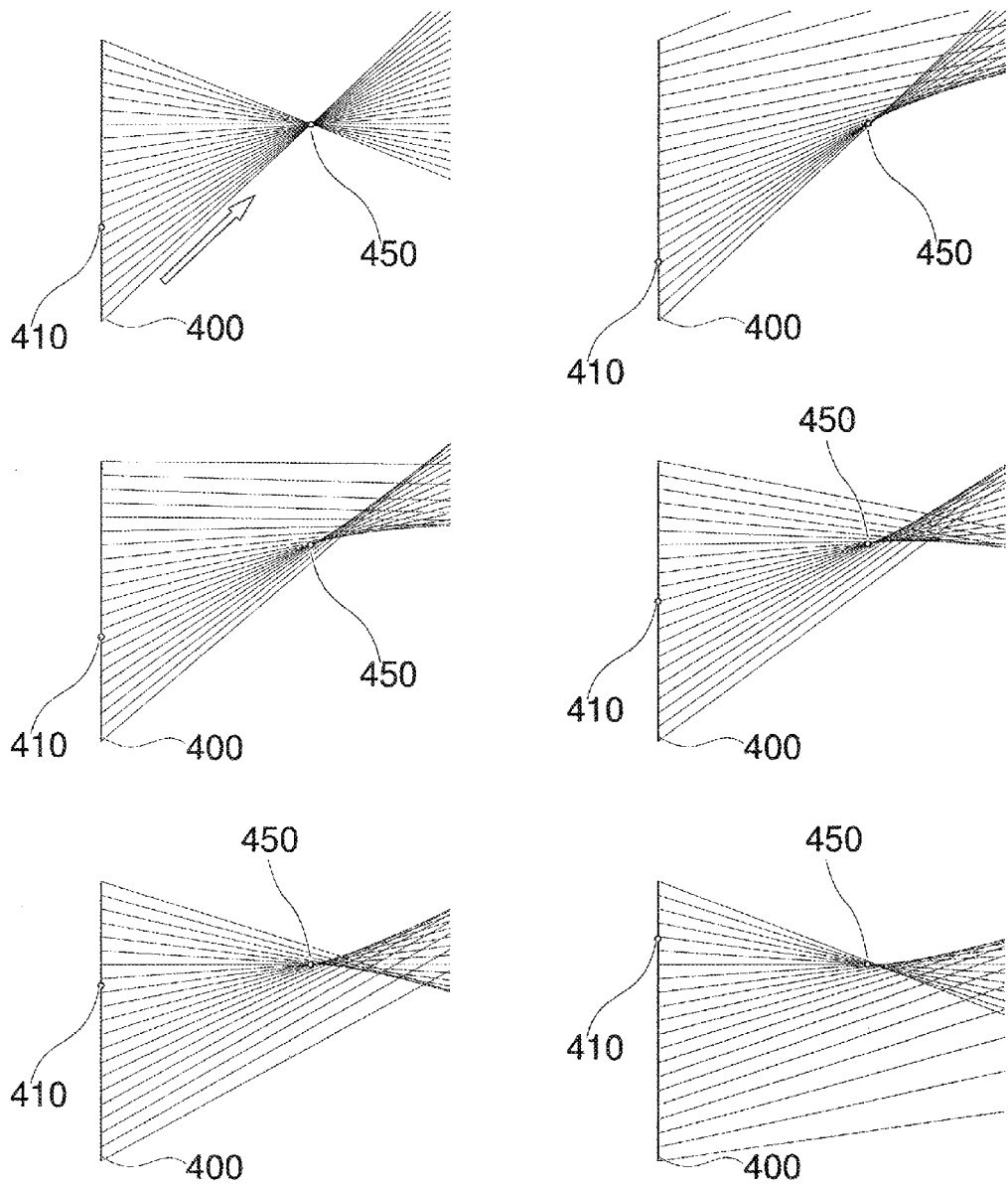
FIG. 4 shows similar results to FIG. 3, different in the coefficients of immediately higher order than those matched.

At a particular point in the line array 200, identified as 310 in various examples in FIG. 3, the first derivative with respect to line position A of the emission timing function T(A) fixes the angle of the wavefront, and hence the direction of the ray from that point. (In an inhomogeneous medium, the ray may curve thereafter.) For a two dimensional array of emitters, matching this requires adjusting two first partial derivatives at the point 310. The line 300 and the point 350 in FIG. 3 (all variants therein) correspond to the line 200 and the focus point 250 in FIG. 2, which is redrawn as the upper left case in FIG. 3. The second derivative of the emission timing function T(A) determines the curvature of the wavefront, and hence the distance along the ray from the point 310 to a point (if any) at which rays 'infinitesimally close' to the ray from the point 310 cross it, causing elevated and/or high intensity. For a two dimensional array of emitters, matching this requires adjusting three second partial derivatives at the point 310. The result is not a perfect focus at the point 350 unless all rays cross at this point, but if a different signal timing function has the same first and second derivatives at the point 310, then the wave propagation has a 'caustic' (so called because the associated high intensity can burn, if the waves carry energy) at the same point 350 as where the original wave geometry had a focus. In the two-dimensional homogeneous case this point 350 is simply the center of curvature of the wavefront. In general the geometry is more complex, but the point 350 of 'infinitesimal focus' for rays beginning near the point 310 is still determined by the first and second derivatives of the emission timing T(A) as mentioned above. (A special case of this, often treated in the textbooks, is the 'paraxial approximation' where the chosen ray follows the axis of symmetry of a focusing system.) If the third derivative at the point 310 also agrees with that for the 'perfect focus' at the point 350, matching four third partial derivatives at the point 310, we have a further increase in intensity at the point 350. It is understood that the position of a transmitter is generally situated in three dimensional space, along a 1-dimensional array in the examples shown, and over a two-dimensional array in the intended embodiment, and so with respect to array position there are one first partial derivative in the first case and two in the second, two and four second partial derivatives respectively, and so on. The single first derivative (the best linear approximation at the point considered) of T(A), for a 2D array coordinatised by a and b, is given by a 2×1 matrix of partial derivatives, $[\partial T/\partial a \ \partial T/\partial b]$. There is a single second derivative—the best quadratic approximation to the difference between T(A) and its linear approximation—which is best given by a symmetric 2×2 matrix, with entries the various second partial derivatives like $\partial^2 T/\partial a^2$ and $\partial^2 T/\partial a \partial b$. The third derivative can be given by a 2×2×2 array, with entries the various third partial derivatives. Equality of $k^{th}$ derivatives is computationally equivalent to equality of all $k^{th}$ partial derivatives, provided that the complete derivative exists (which is not technically guaranteed by the existence of the partials). The surrounding caustic geometry is determined by higher order terms: FIGS. 3 and 4 both show typical cases where the fourth derivative at the point 310 (respectively, 410) is the first to differ from the corresponding derivative in the perfect focus case; the differences have one sign in FIG. 3, the opposite sign in FIG. 4.

For almost all values, the result is a cusped caustic region or "caustic" for short. The cusp point remains at the same point 350 or 450, but the focus is gone. A focus is unstable against perturbations, with an infinite hierarchy of potential 'aberration' effects. A key step in the present invention is that rather than seeking to remove such aberrations from an 'ideal' focus, we treat the characteristic caustic structures as primary objects for manipulation. Enough care can keep aberrations small in a designed refractive system, but if the waves are passing through a region of unknown variation in refractive index, they are much harder to control. 'Perfection' of a focus requires that all derivatives, to arbitrarily high order, match that of the ideal case. An arbitrarily small perturbation of such a singularity results in many terms of lower order, with correspondingly complex aberrations, but a low order singularity cannot generate a higher order one without larger perturbation. For example, a function of the form $x^5$ when perturbed in a generic fashion (as in altering the graph of the function slightly), generates terms of all the lower orders, though the $x^4$ term merely shifts the location of the singularity, and the constant term is often irrelevant to the application (in the present case, it would shift only the time of arrival), but the linear and quadratic terms strongly modify the geometry and intensity of the wave. If we perturb a 'good' focus we cannot control the lower order singularities that can occur. But if we wish to retain a hot spot (infinities of intensity in ray theory) that starts as a lower order singularity like the cusp, it can be stable against perturbations: it will move a little, but not change the differential structure, if the perturbation is small. (Two singularities have by definition the same differential structure, for present purposes, if there exists a smooth invertible local change of variables which reparameterizes each as a form of the other. The mathematics of this has been worked out and available since at least the 1970's and is part of singularity theory, and is often identified as "catastrophe theory.")

By perturbations that do change the first and/or second derivatives at the chosen point, we can move the cusp point in a controlled fashion, since it continues to exist. By perturbations that change only the next higher order derivatives, we can influence the cusp direction, and hence (in the case of acoustic driving of material flow) we have more control over its effects than we have for the 'perfect focus.' Since even small changes in the timing function destroy a perfect focus point, we cannot compute where the small changes move it, unless we have the full knowledge of the medium, and such knowledge is rare outside the homogeneous case of manufactured refractive systems: unless we enforce the infinitely many restrictions that create a focus, the focus goes where the fist goes when the hand opens. The stable, manipulable singularity is a superior tool for the management of high intensity points, where (in the wave description of the physics) constructive self-interference of the wavefront is high.

In an incompletely known inhomogeneous medium, we cannot compute a priori, even for a stable singularity, what signal timing will place the singularity at a desired point. However, the timing measurements already discussed can reveal the 'perfect focus' signal for any point at which a transducer can be placed, and this gives us a class of signals which stably create a singularity (hence a small region with higher intensity than at nearby points, which has computable features in both the wave description and the ray theoretic limit) at that point. If we have such data for several points, we can interpolate and extrapolate from these signals to create singularities of the same type, at intermediate or surrounding points. The correspondence between the signal and the singularity location is non-linear but (for stable singularities) smooth, so that from known points we can construct an approximate inverse with a high expectation of accuracy, which is not available for fragile structures such as a perfect focus.

This capability of navigating the high intensity points is much less present for the Green function approach above, in the case where it uses a single emitter at a point A. Time reversal measurements allow one to construct a signal which (by reversing all the reverberations in the skull) results a focus at a chosen point P in the brain or other medium, at which a transducer is physically placed. Similarly, one can construct the signal for another point Q, at some distance from P. However, a weighted average of these signals, emitted from the point A, is simply superposition of them. Unless the two signals are similar enough to have substantial interference (constructive and destructive) between them, the intensity of the superposition is approximately the superposition of the separate intensities, so that as the weight moves from the P function to the Q function, the hot spot wanes at P and brightens at Q, without the appearance of a moving hot spot between them. A moving spot does appear when we use an array of emitters, but this involves in an essential way the interference between neighbors in the array, and requires the analysis of caustics as disclosed here. The Green function for an intermediate focus is not linearly intermediate between the Green functions for the points P and Q, which thus do not provide control of the kind disclosed above.

Figure 5:
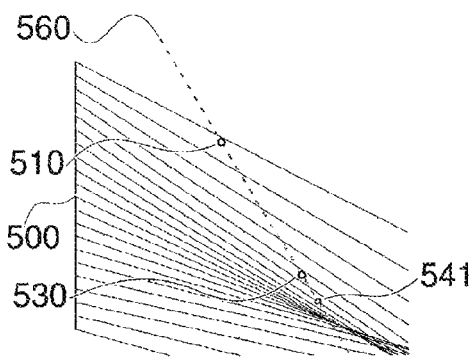
FIG. 5 shows a curved arc of cusp points when the signal timings are interpolated linearly between the signals derived from expansion matching of empirically derived signal timings at two distinct points.
Figure 5:
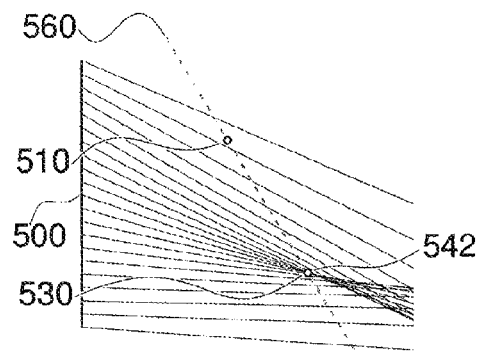
Figure 5:
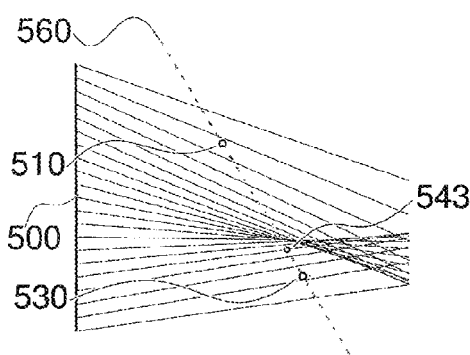
Figure 5:
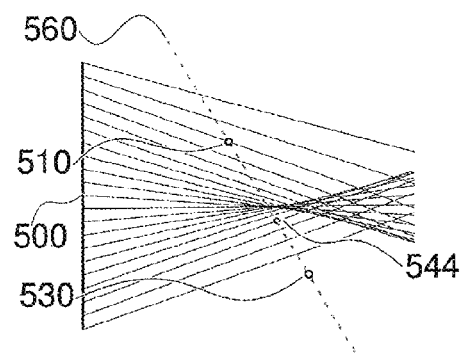
Figure 5:
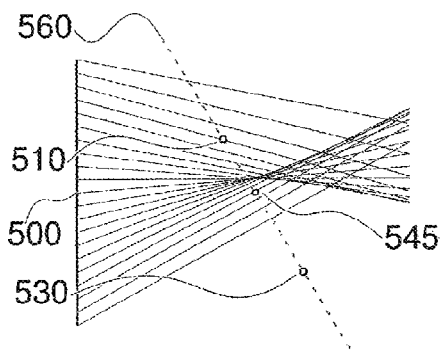
Figure 5:
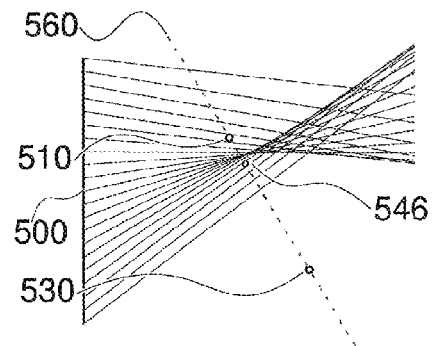
Figure 5:
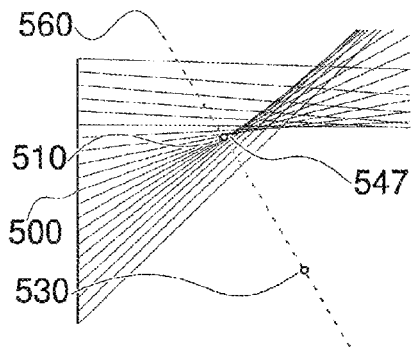
Figure 5:
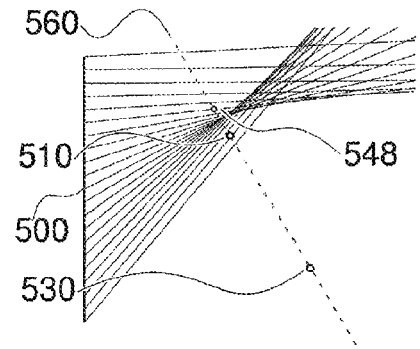

FIG. 5 shows a line 500 of emitters and two points 510 and 530 for which correct 'perfect focus' signal timings are known, from which are derived polynomial timings which give cusped hot spots at exactly those points. If we choose a number w and replace each coefficient by w times the value it has in one polynomial, plus (1−w) times the value it has in the other, the resulting new polynomial gives a cusp at a new point. The points 542 and 547 are the cusp points that occur for the weights w=0 and w=1 respectively, so that they coincide exactly with the original points 510 and 530 for which data was collected. The other cusp points, using this interpolation scheme, lie close to the line through the points 510 and 530, but they do not fall on the points 541, 543, 544, 545, 546, or 548 found by taking w times the coordinates of point 510, plus (1−w) times the coordinates of point 530. The relation between polynomial coefficients and cusp locations is non-linear. It is, however, smooth, so that estimating the weight w to give a desired point on the curve is a practicable task. With time-reversed focus data from more points, a thick region of targets becomes navigable.

It is a claimed inventive step that we are finding in various ways a parametrized approximation to the time delays within a finitely parametrized family of functions (of the position of the transmitters in the array). In the simple case of FIGS. 3, 4 and 5, the functions T(A) are cubic polynomials $b*A^3+c*A^2+d*A+e$ in the position A of the transmitters along the line 300 or 400: a family of functions each of which can be specified by four coefficients, which are the said parameters in this case, The coefficients can be chosen by matching derivatives of the timings T(A) at a chosen point A. This four-dimensional space of candidate signals is much more computationally tractable than the space of all possible signals, unavoidable in manipulating a perfect focus. Within the spirit of the present invention we may use other finite-coefficient-set families of functions (such as low-order trigonometric polynomials, exponentials, etc.), provided that they have enough variability to allow the necessary derivative matching, and few enough parameters for convenience in inverting the correspondence between parameter set and caustic placement.

In 3D we may use low-order polynomials in the (x,y,z) coordinates of the array points, linear combinations of low-order spherical harmonics, and so on, to form a finitely parametrized family of functions from which to choose the timing function T(A) to create the hot spot like the caustic. The parameters are then the polynomial coefficients, the weighting given to the harmonics, or whatever is used in specifying a member of the chosen family of functions T(A). This approach of using a finite family of candidate functions for T(A) works even for inhomogeneous media, where the rays follow curved paths, because the mathematics of these structurally stable singularities applies equally in a smoothly inhomogeneous medium (technically, in a Riemannian manifold). Even in a dissipative medium, where the acoustic waves are damped or attenuated, the same results apply. As long as the model of wavefront propagation along rays remains applicable, the stable singularities retain their form, and are the same as in the straight rays in a homogeneous medium that we have illustrated. The actual positions of these singularities does depend on the details of the medium, and if we move far enough away from one of these caustics, we may enter the neighborhood (in the space of possible forms, rather than in physical space) of another caustic structure, but the singularities as well as their associated diffraction patterns remain stable when we move from the simple homogeneous medium picture to the inhomogeneous or slightly dissipative medium. Inhomogeneities of the transmission medium that are not smooth on the scale of the wavelengths create effects not covered by this scheme. When the wavelength is extremely large compared with the characteristic distances in the medium, the ray picture itself becomes invalid, and there are no hot spots or strong foci to begin with.

Another inventive step within the generic process that we describe is to get the hotspot in the same position as the focus that we obtain from previously described time reversal methods. To do so, we arrange the hotspot in the same position as the focus to fit the parameters in the low-dimensional space of timing functions that we use, so that both the first and second order derivatives of the timing with respect to position in the array (at some specific position in the array) agree with our estimate of those derivatives for the empirically obtained signal timing obtained by the time reversal method.

We can better push material in a given direction, if we control the direction of the propagation at the hot spot 350, which in two dimensions will be along the ray through the cusp point itself, as is clear in FIGS. 3 and 4. The step just discussed allows us to choose this direction by choosing the emitting point of the array at which we match the derivatives as described above.

We have discussed an inventive step that allows us to create structurally stable hot spots in contrast to the unstable foci that result in a highly resolved signal processing method using time reversal. We now describe the apparatus and method required to steer such hot spots within an inhomogeneous medium. It is an inventive capability that we steer hot spots obtained by creating a mathematical transformation K which maps a set of positions within the medium to the positions of the transmitters in the array. We do this by gathering timing data relating two or more points P, Q, . . . within the medium to points in the array. We approximate each timing function $T_P(A)$, $T_Q(A)$, . . . thus experimentally found, that would give perfect focus at the point P, or Q, or . . . by a function $F_P(A)$, $F_Q(A)$ from our finitely parametrized family that gives a hot spot at the points P, Q, . . . respectively, as described in the previous step. At the point P, the value of the said transformation K must be a parameter set which matches (to a functionally sufficient approximation that enables focusing, movement or control of the hot spot) the parameter set giving $F_P(A)$. The new mapping K will thus be an interpolation or smoothing in that it must approximate the known parameters at the internal points P, Q, etc., as illustrated in FIG. 5 for a one-dimensional family of functions F(A) linearly interpolated between those that give 510 and 530 as cusp points. . . . By weighted linear interpolation between three functions that give cusps at three points P, Q and R we can move the resulting cusp more freely than along a curve, while placing it exactly at those three points by concentrating the weights appropriately. In general we can use a larger plurality of points for which parameters are known. Since the straight line in parameter space that describes interpolation between the parameter sets for P and Q consists of points which correspond under K to points not evenly spaced along a straight line in the medium, the mapping K is not linear, but our use of stable structures makes it smooth enough to be (over a substantial region) invertible. Further, if we can observe or track the hotspots, we know for the points P', P", etc., where we find them the values that K(P'), K(P"), etc., actually take: we can then mathematically improve our approximate inverse $K^{-1}$ to the transformation so that the approximate inverse can better direct the hotspot to a desired location. Since are working outside linear transformations (for which an inverse exists globally if the determinant is non-zero, and not at all otherwise), we must sometimes make do with a local inverse: the difference is illustrated by the way that y=3x has the global inverse x=y/3, but y=sin(x) has only the inverse x=arcsin(y) for a limited range of y and x. A wide range of methods for finding such an inverse are well known to those skilled in the art: our preferred first embodiment will use thin plate spine functions (see Bookstein, F. L. "Principal Warps: Thin Plate Splines and the Decomposition of Deformations." *IEEE Trans. Pattern Anal. Mach. Intell.* 11, 567-585, 1989 and the literature citing this paper), since these are convenient in cases where a number of points are required to correspond exactly to other specified points, but any such method may be used within the spirit of the present invention. A simpler scheme, that may be sufficiently accurate in the case of small movements of hot spots in a limited region, is to find the least-squares-error linear correspondence between known hot spot locations and points in the space of timing function parameters (such as the coefficients of the polynomials used) that give timing functions which result in hot spots at the respective locations.

We further illustrate both a) multiple cusps that may appear when we transmit, as well as b) the location of points on the arc depending on the positions P, and Q where we may obtain a focus by time reversal methods or a structurally stable hot spot by the methods described above.

We now illustrate some differences between directional and "non-directional" hot spots.

Figure 6:
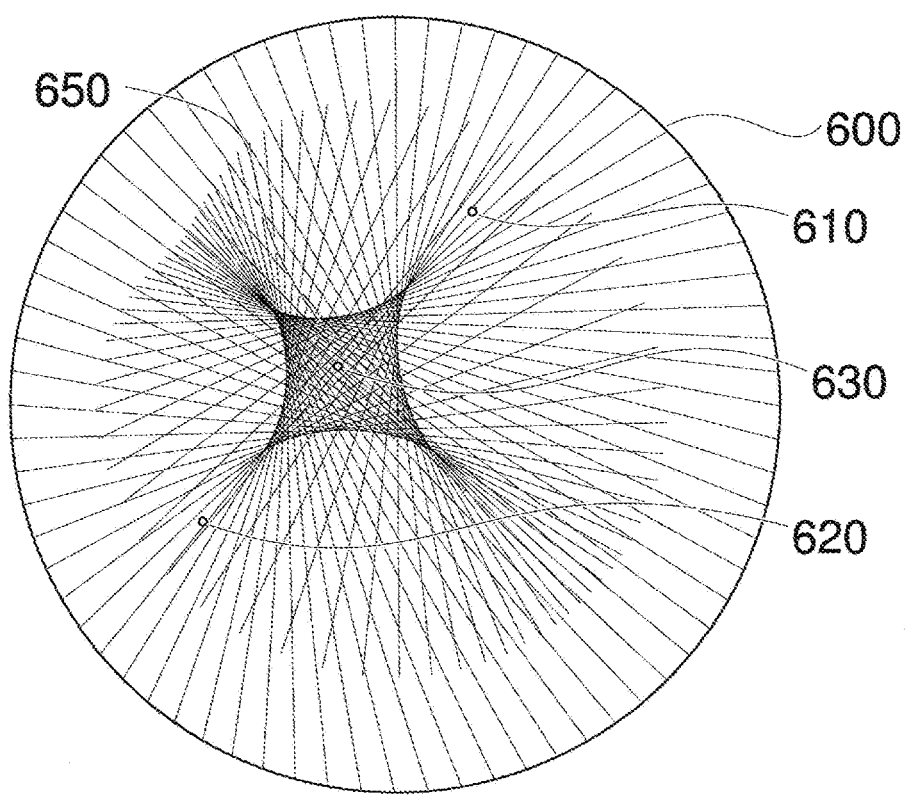
FIG. 6 shows a multiplicity of caustics, for a signal interpolated between signals found by time reversal and not approximated by derivative matching, where the transmission occurs over an entire circle surrounding the two points in question.

FIG. 6 shows a caustic pattern that results from transmission by an array 600 of transmitters entirely surrounding the medium, interpolating between the signals derived directly from the recording phase that allows, by time reversal, the creation of a perfect focus at the point 610 (as in FIG. 1) and for a perfect focus at the point 620. The rays are shown complete from the transmission points, but are broken beyond the hotspot. The result is not a focus at the intermediate point 630, but the complex pattern 650 shown, illustrating the difficulty of navigating with perfect foci. The pattern of cusp points shown may serve to contain material within a region but will not be effective in pushing material in a given direction in a continuing fashion.

Figure 7:
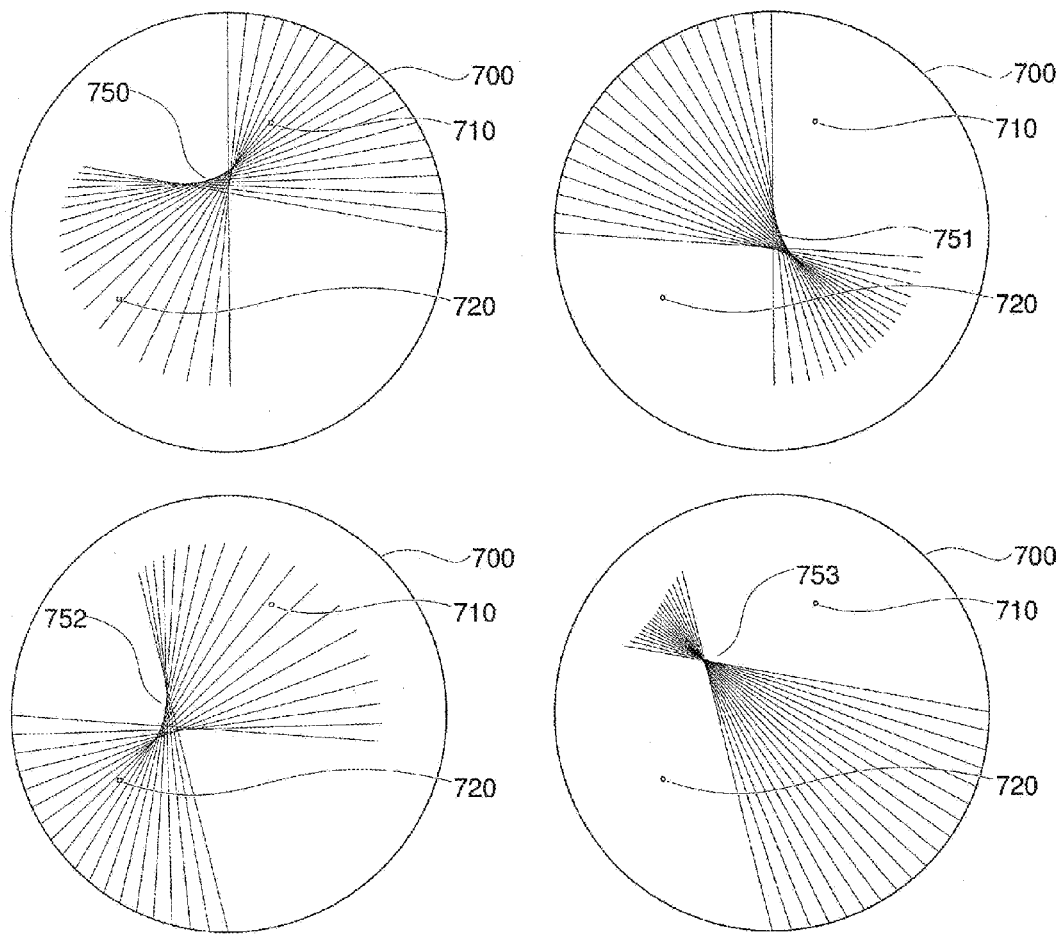
FIG. 7 shows the position of a hot spot created by interpolation as in FIG. 6, as a function of the quadrant from which the waves are propagated.

FIG. 7 illustrates the same interpolation as in FIG. 6 between signals appropriate for a perfect focus at points 710 or 720 (identical to the previous points 610 and 620), when the array of transmitters is restricted to a particular quadrant of the surrounding surface 700 of the medium (a curve 700 is the surface surrounding a plane region in this two-dimensional example), resulting in different cusped hot spots 750, 751, 752 and 753. If the medium is surrounded by a reflective material, such as the skull for the brain, the rays can be reflected again (not shown) through many points including the hot spot shown. These reflections will pass through the cusp point 750, 751, 752 or 753 in different directions, and thus will somewhat reduce the net directional force that we may want to create at those points, in the acoustic driving of material flow, but typically the reflected rays will not be focused (even caustically) at the initial hot spot, so that even without attenuation the effect is limited. If dissipation is also significant, the reflected acoustic waves will have extremely low intensity at the hotspot, so that the strong signal that pushes material is preserved.

Figure 8:
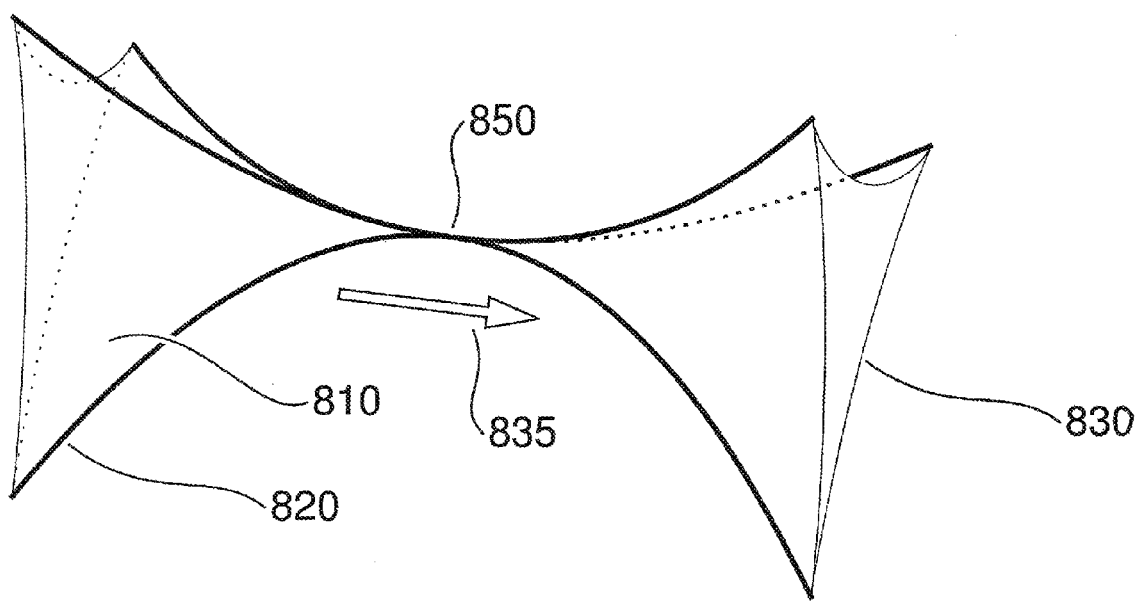
FIG. 8 shows a typical stable caustic form in three dimensions, analogous to the cusps in the two-dimensional figures above.

In contrast to the two-dimensional illustrations shown for clarity in FIGS. 1 to 7, in practice the methods here disclosed are to be used in three dimensions, resulting in caustics somewhat more complex than those shown in the figures. The symmetry of a spherically perfect focus is most easily perturbed into the three-fold symmetric caustic shown in FIG. 8. The figure shows a stable surface form 810 where the intensity increases (compared to the surroundings) in a manner comparable to that along the curves emanating in 2D from a cusp, with cusped ridges 820 where the intensity is greater, and a maximum intensity point 850. (The arrow 835 indicates the general direction of the energy and momentum transport by the rays or waves.) This caustic form is known as an 'elliptic umbilic': two other structures (the 'swallowtail' and 'hyperbolic umbilic') also occur stably in three-dimensional caustics, but this one is the most common for the present application, and serves to illustrate the nature of stable three-dimensional hot spots.

An alternative description of methods used in the practice of this technology, including some exegesis of the steps described, is as a method and system to select and modify localized regions of intensity in waves transmitted through a space occupied by a first inhomogeneous medium using at least the steps of:

(a) Placing a plurality of transducers in a fixed array adjacent to the said space;
(b) Placing at least one transducer within the space;
(c) Causing the travel of a pulse between each of the at least one transducers within the space, at least one location for each transducer, for a plurality of locations overall, and each transducer in the said fixed array;
(d) Recording the time for the leading edge of each such pulse to travel between each transducer in the said fixed array and each of the transducers within the space, at each location within the space used;
(e) Creating a data structure (e.g., graph or look-up table) containing the recorded times of each pulse between each of N transducers in the array and each location of each transducer within the space (the data collection used in creating the data structure may use a pulse in either direction, though emission from within the space is our preferred embodiment) as a function of the position of the transducer in the array;
(f) Fitting to each data structure in step (e) a geometric form defined by a number M fewer than N of parameters within a fixed family of such forms (such as, but not limited to, a polynomial with fewer than N coefficients, belonging to the family of such forms) as an approximation that lies near each data point recorded in the said data structure; and
(g) Generating pulses from the transducers on the array based on the approximation generated in step (f) so that the N pulse emissions result in a stable pattern of intensity points, the said pattern being other than a single focus.

In this method, N may represent at least 12 transducers and the approximation is created using only four parameters or at least 12 and up to 100 transducers and the approximation is created using only four parameters. The number N of parameters must suffice to match (at a chosen point in the array) the first, second and third derivatives of the approximation. In a array distributed over a surface the first derivative requires 2 distinct numbers (partial derivatives) to specify it, the second requires 3, and the third requires 4, so M must be at least 9. Additional parameters (such as the 5 coefficients of fourth-order terms) can provide additional control of the caustic form, provided that N is large enough that M remains smaller.

In this method, after the approximation is created using the first inhomogeneous material, an operator may generate pulses from the transducers on the array in a second inhomogeneous based on the approximation generated in step (f) so that all N pulse emissions are not focused on a single point. Also, and optionally, the fitting in step (f) may be performed by choosing the geometric form guided by the field established and conventional mathematical methods and results of singularity theory and catastrophe theory, resulting in a form that is structurally stable against smooth perturbations of the medium properties and other smooth changes of conditions under which the data points were obtained.

To summarize, we have described a method and system to select and modify localized regions of high intensity in waves transmitted through a space occupied by an inhomogeneous medium comprising the steps of:

(a) Placing a plurality of transducers in a fixed array adjacent to the said space;
(b) Placing at least one transducer within the said space;
(c) Causing the travel of a pulse between each transducer within the space, at least one location, for a plurality of locations overall, and each transducer in the said fixed array. (In this step, our general preferred embodiment uses a pulse emitted at the location within the space: timing can then be handled in parallel across processors in the array, without waiting for echoes to die. But if in a particular embodiment a transmitter is not convenient, for reasons particular to that embodiment, a receiver is an acceptable alternative.);
(d) Recording the travel time of the leading edge of each such pulse. (The arrival of the pulse emitted in Step (c) can in general can be smeared out by echoes, so that we must be precise in defining "arrival time": that of the leading edge.);
(e) For each location used within the space, finding an approximation, within a fixed family finitely parametrized (by coefficients in a family of polynomials or trigonometric polynomials, weights multiplying different spherical harmonics before adding them, etc.), of functions of transducer position(s) in the array, to the travel time between the said location and the transducers in the fixed array;
(f) Constructing a mathematical transformation from locations within the space to sets of function parameters as used in the said fixed family of functions of transducer position(s) in the array, that approximates the sets of function parameters found in the previous step for actual locations;
(g) Constructing a computable approximate inverse to the said transformation (as previously described herein);
(h) Using the said computable approximate inverse to specify, for a fixed or moving point in the said space, signals so constructed such that when emitted from an array co-located with or identical to the said transducer array, they will cause localized high intensity around the said fixed or moving point; and (i) Emitting such signals.

In Step 1e, such a family of functions may consist of polynomials in variables (u, v) used to specify the location of individual members of the array, or (for the case of an array wrapped onto a region of a sphere) a combination of spherical harmonics up to a selected finite degree, or any other convenient finite-dimensional family of scalar functions. The simplest example of a fixed family of polynomials is to use only linear functions au+bv+c of (u, v), though this is not sufficient for the matching described, which would in the polynomial case need to adjust also the coefficients of $u^2$, uv, $uv^2$, $u^3$, $u^2v$, $uv^2$, and $v^3$. As an example of the approximate transformation, the least-squares linear fit of the coefficients a, b and c as a function of the focus location (X, Y, Z) within the space may be used: our preferred embodiment, however, uses a higher-order polynomial mapping to a larger space of candidate functions.

In Step 1g, linear interpolation between the functions known to give high intensity at particular locations approximately inverts the linear-fit model of a, b and c as a linear function of the within-space location (X, Y, Z). However, we prefer a higher-order approximation to the dependence of a larger set array time function parameters on the change with location (X, Y, Z) of the parameter values. This is expected to give a better approximation to actual time array functions, and (within the region for which an inverse exists) a better choice function for parameter values that direct the hotspot to a desired point. Although specific techniques, compositions, materials, equations and steps have been described in this description, these are specific examples enabling a generic concept represented in the claims. The claims and description should therefore not be taken as specifically limiting the scope of the claims.

The invention claimed is:

1. A method for selecting and modifying localized regions of intensity in waves transmitted through a space occupied by an inhomogeneous medium comprising the steps of:
   (a) Placing a plurality of transducers in a fixed array adjacent to the space;
   (b) Placing at least one transducer within the space;
   (c) Causing a pulse to travel between each of the at least one transducers within the space, at least one location for each transducer for a plurality of locations of transducers, and each transducer in the said fixed array;
   (d) Recording in a processor having memory time for a leading edge of each such pulse to travel between each transducer in the said fixed array and between each of the transducers within the space, at each location within the space;
   (e) For each location of each transducer used within the space, the processor executing code to find an approximation, within a fixed finitely parametrized family of functions of transducer position in the array, of the travel time between each location of the said transducer within the space and between the transducers in the fixed array;
   (f) The processor executing code to construct a mathematical transformation from locations within the space to sets of function parameters of the form used to identify points in the said parametrized family of functions of transducer position in the array, the mathematical transformation giving a set of function parameters for each possible location within the space including at least one location other than a location of a transducer, with the set given for each location within the space that is used in the third step being a set that approximates the set of function parameters found for the said location in step (e);
   (g) The processor executing code to construct a computable approximate inverse to the transformation;
   (h) The processor executing code to use the computable approximate inverse to specify, for a fixed or moving point in the said space, signals constructed such that when such constructed signals are emitted from an array co-located with or identical to the said transducer array, the constructed signals cause localized maxima of intensity at or near to the said fixed or moving point; and
   (i) Emitting such constructed signals from the fixed array as provided by the processor from memory, and said constructed signal including emission directed at the at least one location other than a location of a transducer.

2. The method according to claim 1, where the waves are acoustic waves.

3. The method system according to claim 1, where the waves are electromagnetic waves.

4. The method according to claim 1, where the signal from each transducer in Step h is a pulse emitted at a time chosen according in Step g.

5. The method according to claim 1, where a region of high intensity in the emitted constructed signals in step i) is used to direct a flow of material.

6. The method according to claim 5, where wave intensity of the emitted constructed signals alters flow of the material within a living body.

7. The method according to claim 1, where the material is in a region of inhomogeneous geology.

8. The method according to claim 1, where the material is in an industrial plant requiring the flow of material.

9. The method according to claim 1, where the region of intensity is used to modify a local property of material.

10. The method according to claim 9, where the local property is viscosity.

11. The method according to claim 9, where the local property is temperature.

12. The method according to claim 9, where the local property is biological viability.

13. The method of claim 1 wherein the parameterization of functions for approximation of step (e) is performed by execution of code by the processor with thin plate spline functions where a number of locations within the space are approximated to correspond exactly to other specified locations within the space.

14. The method of claim 13 wherein a processor in communication with the emitters executes code on incoming information to:
   (i) Record the time for the leading edge of each such pulse to travel between each transducer in the said fixed array and between each of the transducers within the space, at each location within the space;
   (ii) Find the approximation, within the fixed finitely parametrized family of functions of transducer position in the array, of the travel time between each location of the said transducer within the space and between the transducers in the fixed array;
   (iii) Construct the mathematical transformation from locations within the space to sets of function parameters of the form used to identify points in the said parametrized family of functions of transducer position in the array;
   (iv) Construct the computable approximate inverse to the transformation;
   (v) Use the computable approximate inverse to specify the signals constructed such that when such constructed signals are emitted from an array co-located with or identical to the said transducer array, the constructed signals cause localized maxima of intensity at or near to the said fixed or moving point; and (vi) Direct emitters to emit such constructed signals from the fixed arrays, said constructed signal including emission directed at multiple locations other than a location of a transducer.

15. The method of claim 1 wherein a processor in communication with the emitters executes code on incoming information to:

(i) Record the time for the leading edge of each such pulse to travel between each transducer in the said fixed array and between each of the transducers within the space, at each location within the space;

(ii) Find the approximation, within the fixed finitely parametrized family of functions of transducer position in the array, of the travel time between each location of the said transducer within the space and between the transducers in the fixed array;

(iii) Construct the mathematical transformation from locations within the space to sets of function parameters of the form used to identify points in the said parametrized family of functions of transducer position in the array;

(iv) Construct the computable approximate inverse to the transformation;

(v) Use the computable approximate inverse to specify the signals constructed such that when such constructed signals are emitted from an array co-located with or identical to the said transducer array, the constructed signals cause localized maxima of intensity at or near to the said fixed or moving point; and (vi) Direct emitters to emit such constructed signals from the fixed arrays, said constructed signal including emission directed at multiple locations other than a location of a transducer.

16. The method according to claim 1, where the signal from each transducer in Step h is a continuous wave whose phase as a function of time and transducer location is chosen in Step g.

* * * * *